United States Patent [19]

Commons et al.

[11] 4,394,504

[45] Jul. 19, 1983

[54] CEPHALOSPORIN DERIVATIVES

[75] Inventors: Thomas J. Commons, Wayne; John R. Potoski, Spring City, both of Pa.

[73] Assignee: American Home Products Corporation, New York, N.Y.

[21] Appl. No.: 309,361

[22] Filed: Oct. 7, 1981

[51] Int. Cl.³ .......................................... C07D 501/34
[52] U.S. Cl. ...................................... 544/28; 544/22; 544/25; 544/27; 548/246
[58] Field of Search ...................... 544/22, 25, 27, 28

[56] References Cited

U.S. PATENT DOCUMENTS 3,971,778 7/1976 Cook et al. ........................... 424/246
4,024,133 5/1977 Cook et al. ........................... 424/246
4,033,950 7/1977 Cook et al. ........................... 424/246

FOREIGN PATENT DOCUMENTS 1464377 2/1977 United Kingdom .
2018247 10/1979 United Kingdom .

OTHER PUBLICATIONS

Hagawara et al., J. Med. Chem. 1980, 23, 1108–1113.

*Primary Examiner*—Paul M. Coughlan, Jr.
*Attorney, Agent, or Firm*—Richard K. Jackson

[57] ABSTRACT

7-[2-(3-Amino-5-isoxazolyl)-2-alkyloxyiminoacetamido]-ceph-3-em-4-carboxylic acid derivatives are antibacterial agents effective against gram-positive and gram-negative bacterium.

3 Claims, No Drawings

CEPHALOSPORIN DERIVATIVES

DESCRIPTION OF THE INVENTION

In accordance with this invention there is provided a group of novel 7-acylamidoceph-3-em-4-carboxylic acid derivatives of the formula:

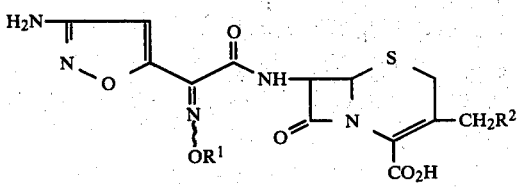

in which
R$^1$ is hydrogen, alkyl of 1 to 4 carbon atoms, alkenyl of 2 to 4 carbon atoms, alkynyl of 2 to 4 carbon atoms, arylalkyl of 7 to 10 carbon atoms, 2-carboxyprop-2-yl, carboxymethyl, alkanoyl of 2 to 4 carbon atoms or α-phenylalkanoyl of 8 to 10 carbon atoms;

R$^2$ is hydrogen, hydroxy, alkanoyloxy of 2 to 6 carbon atoms, carbamoyloxy,

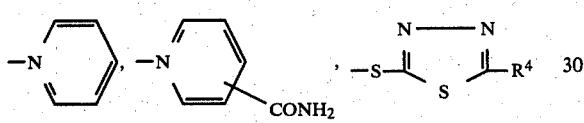

where
R$^4$ is hydrogen or alkyl of 1 to 4 carbon atoms or

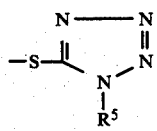

where
R$^5$ is hydrogen, alkyl of 1 to 4 carbon atoms, vinyl, sulfonyloxymethyl, carboxymethyl;
or a pharmaceutically acceptable salt thereof.

The alkyl substituents present in the compounds of this invention are selected from the group consisting of methyl, ethyl, propyl, isopropyl, butyl and isobutyl. Similarly, the alkenyl groups contemplated are vinyl, allyl, isopropenyl and 3-butenyl while the alkynyl groups may be ethynyl, 2-propynyl, 2-butynyl or 3-butynyl. The arylalkyl groups embrace the benzyl, phenethyl, phenpropyl, xylylmethyl, cumenylmethyl, and the like. The alkanoyl groups embrace acetyl, propanoyl, butanoyl, isobutanoyl, and the like.

The pharmaceutically acceptable salts embrace acid addition salts, where applicable or alkali metal, alkaline earth metal or amine salts of the free carboxylic acid. Examples of acid addition salts include both organic and inorganic non-toxic salts formed with acids such as hydrochloric, hydrobromic, sulfuric, phosphoric, methane sulfonic, nitric, p-toluene sulfonic, acetic, citric, maleic, succinic acid and the like. The alkali metal, alkaline earth and amine salts of the 4-carboxyl group include sodium, potassium, lower alkylamine (e.g. methylamine, ethylamine, propylamine, etc.), di(lower)alkylamine (e.g. dimethylamine, diethylamine, dipropylamine, etc.), di(hydroxyethyl)amine, N,N'-dibenzylethylenediamine, and the like.

The cephalosporin derivatives of this invention are prepared by conventional acylation of 7-aminocephalosporanic acid (4-carboxy protected) with 2-(3-protected amino-5-isoxazolyl)-2-oxy-imino-acetic acid followed by removal of the amino and carboxy protecting groups. The protecting groups employed are those conventionally employed in the penicillin and cephalosporin arts to prevent reaction with undesirable substituents present in either 7-ACA or the acylating reactant. The substituents in 3-position may be present prior to acylation of the 7-amino group or introduced subsequently by displacement of its acetoxy substituent.

The 7-acyl moiety of the cephalosporin compounds disclosed herein is derived from the correspondingly substituted novel 2-(5-isoxazolyl)-2-oxyiminoacetic acids, which acid intermediates represent an additional aspect of this invention and present the structural formula:

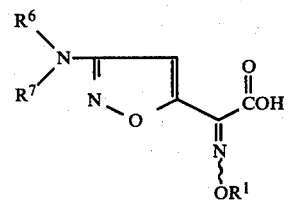

in which R$^1$ is defined above and R$^6$ and R$^7$ represent singly or together an amine protecting group which is easily removable by acid hydrolysis or other well known techniques such as formyl, trifluoroacetyl, o-, p- or 2,4-dinitrophenylsulfenyl, tritylsulfenyl, o-nitrophenoxyacetyl, chloroacetyl, trichloromethylacetyl, γ-chlorobutyryl, benzyloxycarbonyl, p-chlorobenzyloxycarbonyl, p-nitrobenzyloxycarbonyl, p-bromobenzyloxycarbonyl, p-methoxybenzyloxycarbonyl, 2-(p-biphenylyl)isopropoxycarbonyl, diphenylmethoxycarbonyl, tertiary-butyloxycarbonyl, diisopropylmethoxycarbonyl, cyclopentyloxycarbonyl, phenylthiocarbonyl, triphenylmethyl (trityl), benzyl, trimethylsilane, and the like. The preferred amino blocking groups are chloroacetyl, tertiarybutyloxycarbonyl, trityl, alkyloxycarbonyl, cyclopentyloxycarbonyl, tertiaryamyloxycarbonyl and the groups

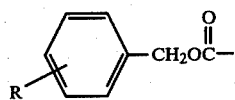

in which R is selected from the group consisting of —H, halo, lower alkoxy and nitro, preferably R is hydrogen.

The 2-(5-isoxazolyl)-2-oxyimino-acetic acid intermediates are prepared from 3-amino-5-methylisoxazole by (1) protecting the 3-amino-substituent, (2) metallation of the 5-methyl group followed by carboxylation to produce the corresponding 3-amino-isoxazol-5-yl acetic acid, (3) protecting the carboxyl group, (4) iodination in 2-position of acetic acid moiety, (5) hydrolysis to the 2-keto acetic acid derivative followed by (6) alkoxyimination of the keto group. Alternatively, the carboxy protected 3-amino-isoxazol-5-ylacetic acid intermediate may be converted to the hydroxyimino derivative by treatment with a base, such as lithium hexamethyldisilazine, followed by reaction with nitrosyl chloride. The product may then be converted to the desired alkoxyimino derivative by alkylation. If desired, the syn- and anti- configurational isomers may be separated by conventional means.

The antibacterial compounds of this invention are effective against gram-positive and gram-negative test organisms at inhibitory concentrations at or below 250 micrograms per milliliter using the well-known and scientifically accepted agar serial dilution technique. Thus, the antibacterial agents of this invention are useful in the fields of comparative pharmacology and microbiology and may be used in the treatment of infections amenable to treatment with cephalosporins and penicillins such as bovine mastitis as well as in the eradication of bacterial colonies outside the animal host.

The following examples are presented for purposes of illustration and should not be construed as limitations upon the true scope of this invention. The biological activity data presented after each example illustrates the compounds activity against specific bacteria of the designated strain in terms of the minimum inhibitory concentration of the compound in micrograms per milliliter to completely inhibit the test organism.

The abbreviations for the bacteria employed in the testing procedure are as follows:

BA SU—*Bacillus subtilis,*
ST AU—*Staphylococcus aureus,*
ES CO—*Escherichia coli,*
EN CL—*Enterobacter cloacae,*
SA PA—*Salmonella paratyphi,*
EN AE—*Enterobacter aerogenes,*
KL PN—*Klebsiella pneumoniae,*
BO BR—*Bordetella brochiseptica,*
PR VU—*Proteus vulgaris,*
PR MI—*Proteus mirablis,*
HE SP—*Herellea species,*
PS AE—*Pseudomonas aeruginosa,*
ES IM—*Escherichia intermedia.*

EXAMPLE 1

3-Tritylamino-5-Methylisoxazole

Triethylamine (10 ml., 71.9 mmol) is added dropwise to an ice cold solution of 20.0 g. (71.6 mmol) of trityl chloride in 200 ml. of methylene chloride and the resulting solution is stirred at ice bath temperature for 5 minutes. 3-Amino-5-methylisoxazole (7.0 g., 71.5 mmol) in 50 ml. of methylene chloride is then added dropwise over 10 minutes. After the addition, the ice bath is removed and the stirring continued for 1.5 hours. The solution is washed with ice cold 1 N HCl, dried (MgSO$_4$) and the solvent concentrated under reduced pressure until a white solid is present. Diethyl ether is added and the solid collected and dried to give 21 g. (85%) of the title compound as a white crystalline material; m.p. 196°-199° C.

IR (KBr) 3310, 1630, 1540 and 1490 cm$^{-1}$
NMR (CDCl$_3$) δ 2.05 (S, 3H); 4.81 (S, 1H); 5.46 (S, 1H); 7.31 (S, 15H).
Analysis for: C$_{23}$H$_{20}$N$_2$O, Calculated: C, 81.15; H, 5.92; N, 8.23, Found: C, 80.75; H, 6.04; N, 8.12.

EXAMPLE 2

3-Tritylamino-5-Isoxazolyl-2-Acetic Acid

N-Butyl lithium in hexane (38 ml. of 0.8 M solution; 32.0 mmol) is added dropwise under nitrogen to a solution of 5.0 g. (14.7 mmol) of 3-tritylamino-5-methylisoxazole in 100 ml. of dry THF at approximately −70° C. and the solution stirred at that temperature for 15 minutes. An excess of CO$_2$ is then added through a drying tube (MgSO$_4$). The CO$_2$—acetone bath is replaced with an ice bath and the stirring continued until all the CO$_2$ is added. The reaction is partitioned between ice cold 1 N HCl—CH$_2$Cl$_2$, extracted, dried (MgSO$_4$) and the solvent removed under reduced pressure. Methylene chloride is added to the residue and the resulting white solid collected by filtration and dried to give 1.52 g. (27%) of the title acid; m.p. 197°-198° C. with loss of CO$_2$.

IR (KBr) 3340, 1715 and 1620 cm$^{-1}$
NMR (D$_6$-DMSO) δ 3.55 (S, 2H); 5.79 (S, 1H); 7.29 (S, 15H).

EXAMPLE 3

Methyl-(3-Tritylamino-5-Isoxazolyl)-2-Acetate

Diazomethane in diethyl ether is added to a suspension of 517 mg. (1.34 mmol) of 3-tritylamino-5-isoxazolyl-2-acetic acid in methylene chloride. The excess diazomethane is destroyed with glacial HOAc and the solution washed with aqueous NaHCO$_3$, dried (MgSO$_4$) and the solvent removed under reduced pressure. Chromatography of the residue on silica gel (60–200 mesh) using CH$_2$Cl$_2$ as an eluent gives the title ester as a crystalline material. Recrystallization from CH$_2$Cl$_2$-diethyl ether give 347 mg. (65%) of the title ester;

m.p. 149.0°-151.5° C.
IR (KBr) 3300, 1745 and 1625 cm$^{-1}$
NMR (CDCl$_3$) δ 3.45 (S, 2H); 3.62 (S, 3H); 5.10 (S, 1H); 5.51 (S, 1H); 7.30 (S, 15H).

EXAMPLE 4

Methyl 2-(3-Tritylamino-5-Isoxazolyl)-2-Iodoacetate

A solution of 100.0 mg (0.251 mmol) of methyl-(3-trityl-amino-5-isoxazolyl)-2-acetate in 5 ml. of dry THF is added dropwise under nitrogen to a solution at approximately −70° C. of 0.522 mmol of lithium hexamethyldisilazane (HMDS) in 5 ml. of THF (prepared from HMDS and 1 equivalent of n-BuLi). After the addition, the solution is allowed to come to room temperature, stirred at room temperature for 15 minutes and then added under nitrogen to a solution at approximately −70° C. of 64.8 mg. (0.255 mmol) of iodine in 5 ml. of dry THF. After the addition the solution is partitioned between ice cold 1 N HCl—CH$_2$Cl$_2$, extracted, washed with aqueous Na$_2$S$_2$O$_3$, dried (MgSO$_4$) and the solvent removed under reduced pressure. Chromatography of the residue on silica gel (60–200 mesh) using 2:1 CH$_2$Cl$_2$:hexane as an eluent gives the title iodoester as a solid foam (54.3 mg., 41%).

IR (KBr) 3400, 1735 and 1605 cm$^{-1}$.
NMR (CDCl$_3$) δ 3.70 (S, 3H); 5.36 (S, 1H); 5.48 (S, 1H); 5.52 (S, 1H); 7.32 (S, 15H).

EXAMPLE 5

Methyl 2-(3-Tritylamino-5-Isoxazolyl)-2-Ketoacetate

A solution of 244.7 mg. (0.47 mmol) of methyl 2-(3-trityl-amino-5-isoxazolyl)-2-iodoacetate in 20 ml. of THF and 10 ml. of water is stirred at room temperature for 6 hours. The reaction is partitioned between aqueous Na$_2$S$_2$O$_3$—CH$_2$Cl$_2$, extracted, dried (MgSO$_4$) and the solvent removed under reduced pressure. Chromatography of the residue on 60 g. of silica gel (60–200 mesh) using CH$_2$Cl$_2$ as an eluent gives the title ketoester as a yellow crystalline solid which is recrystallized from $CH_2Cl_2$-diethyl ether (55.9 mg., 29%); m.p. 174°–175° C.

IR (KBr) 3340, 1735, 1690 and 1590 cm$^{-1}$.

NMR (CDCl$_3$) δ 3.85 (S, 3H); 5.85 (S, 1H); 6.16 (S, 1H); 7.32 (S, 15H),

Analysis for: $C_{25}H_{20}N_2O_4$, Calculated: C, 72.80; H, 4.89; N, 6.79, Found: C, 72.11; H, 4.93; N, 6.75.

EXAMPLE 6

Methyl 2-(3-Tritylamino-5-Isoxazolyl)-2-Methoxyiminoacetate

A solution of sodium methoxide in methanol is added at room temperature, until a pink color persists, to 10.3 mg. (0.12 mmol) of o-methylhydroxylamine hydrochloride in dry MeOH containing a few crystals of phenolphthalein and 3 A molecular sieves. Methyl 2-(3-tritylamino-5-isoxazolyl)-2-ketoacetate (17.8 mg., 0.04 mmol) is then added and the reaction stirred at 65° C. for 5 hours. The sieves are removed by filtration and the filtrate concentrated to dryness under reduced pressure. After chromatography on silica gel (60–200 mesh) using 5:2 hexane:EtOAc as an eluent the title compound is isolated as a mixture of syn- and anti-methyloximes (13.7 mg., 72%).

IR (CHCl$_3$) 3410, 1735, 1610 and 1595 (sh) cm$^{-1}$

NMR (CDCl$_3$) δ 3.80 and 3.85 (S, —NOCH$_3$; syn- and anti-); 3.97 and 3.99 (S, COCH$_3$; syn- and anti-); 5.30 (S, isoxazole ring proton for syn-isomer, Hashimoto et al., J. Med. Chem., 23, 1108 (1980)); 5.62 (S, NH; syn- and anti-isomers); 5.77 (S, isoxazole ring proton for anti-isomer, Hashimoto et al., loc.cit.); 7.30 (S, 30 H, tirtyl protons for syn- and anti-isomer).

EXAMPLE 7 anti-Methyl 2-(3-Tritylamino-5-Isoxazolyl)-2-Hydroxyiminoacetate

A solution of 4.02 g. (10.1 mmol) of methyl-(3-tritylamino-5-isoxazolyl)-2-acetate prepared as in Example 3 in 50 ml. of dry THF is added dropwise under nitrogen over 15 minutes to a solution of lithium hexamethyldisilazane (22.2 mmol) in 100 ml. of THF at dry ice-acetone temperature. After the addition, the cooling bath is removed. When the temperature of the solution is approximately 20° C. it is cooled to dry ice-acetone temperature. A nitrosyl chloride solution (60 ml. of 0.197 M solution in THF, 11.8 mmol) is then added dropwise over 15 minutes. After the addition the solution is stirred at approximately −65° C. for 30 minutes. The reaction is then partitioned between ice water-$CH_2Cl_2$, acidified with 1 N HCl, extracted, dried (MgSO$_4$), and the solvent removed under reduced pressure. When diethyl ether is added to the residue, a solid forms which is collected by filtration and dried to give the anti-oxime (2.94 g., 69%) as a light tan solid.

IR (KBr) 1730, 1595 and 1500 cm$^{-1}$,

NMR (d$_6$-DMSO) δ 3.78 (S, 3H); 6.70 (S, 1H); 7.32 (S, 15H); 7.59 (S, 1H).

EXAMPLE 8 syn-Methyl 2-(3-Tritylamino-5-Isoxazolyl)-2-Hydroxyiminoacetate

The mother liquors obtained from Example 7 are subjected to high pressure liquid chromatography through PrepPAK ®-500/Silica (Waters Associates, Milford, MA) HPLC. Isolation of the faster moving isomer gives the syn-oxime (320 mg., 7%) as a yellow solid foam.

IR (KBr) 1735 and 1595 cm$^{-1}$,

NMR (d$_6$-DMSO) δ 3.81 (S, 3H); 6.13 (S, 1H); 7.31 (S, 15H); 7.58 (S, 1H); 12.73 (S, 1H).

EXAMPLE 9 anti-Methyl 2-(3-Tritylamino-5-Isoxazolyl)-2-Methoxyiminoacetate

A mixture of 974.1 mg. (2.2 mmol) of anti-methyl 2-(3-tritylamino-5-isoxazolyl)-2-hydroxyiminoacetate prepared in Example 7, 710 μl (11 mmol) of methyl iodide, 470 mg. of anhydrous $K_2CO_3$ in 25 ml. of dry DMF are stirred at room temperature for 4 hours. The reaction is partitioned between $CH_2Cl_2$—$H_2O$, extracted, dried (MgSO$_4$) and the solvent removed under reduced pressure. Chromatography of the residue on silica gel (60–200 mesh) using 5:2 hexane:EtOAc as an eluent gives the title anti-methyloxime as a crystalline solid which is recrystallized from $CH_2Cl_2$-diethylether (477.4 mg., 21%); m.p. 147.5°–149.5° C.

IR (KBr) 3290, 1735, 1600 and 1580 cm$^{-1}$.

NMR (CDCl$_3$) δ 3.89 (S, 3H); 4.03 (S, 3H); 5.67 (S, 1H); 5.82 (S, 1H); 7.35 (S, 15H).

EXAMPLE 10 syn-Methyl 2-(3-Tritylamino-5-Isoxazolyl)-2-Methylhydroxyiminoacetate

In the same manner as described for the synthesis of the anti-methyloxime in Example 9 the syn-methyloxime is isolated as a crystalline solid and recrystallized from $CH_2Cl_2$-diethylether (160 mg., 52%); m.p. 172.0°–174.0° C.

IR (KBr) 330 1745 and 1615 cm$^{-1}$.

EXAMPLE 11 anti-2-(3-Tritylamino-5-Isoxazolyl)-2-Methoxyiminoacetic Acid

A mixture of 403.4 mg. (0.91 mmol) of anti-methyl 2-(3-tritylamino-5-isoxazolyl)-2-methoxyiminoacetate prepared in Example 9, 15 ml. of THF, 7 ml. of water and 1.83 ml. (1.83 mmol) of 1 M NaOH are stirred at room temperature for 1.5 hours. The reaction is partitioned between ice water-$CH_2Cl_2$, acidified with 1 N HCl, extracted, dried (MgSO$_4$), and the solvent removed under reduced pressure. Trituration of the residue gives the title compound as a light yellow solid (359.8 mg., 92%).

IR (KBr) 3340, 1710 and 1590 cm$^{-1}$.

NMR (d$_6$-DMSO) δ 4.01 (S, 3H); 6.59 (S, 1H); 7.30 (S, 15H); 7.60 (S, 1H).

EXAMPLE 12 syn-2-(3-Tritylamino-5-Isoxazolyl)-2-Methoxyiminoacetic Acid

In the same manner as described for the anti-isomer in Example 11, the syn- acid is isolated as a white solid (215.9 mg., 82%).

IR (KBr) 3380, 1710 and 1605 cm$^{-1}$.

EXAMPLE 13 tert-Butyl 3-Acetoxymethyl-7-[2-(3-Tritylamino-5-Isoxazolyl)-2-anti Methoxyiminoacetamido]-Ceph-3-em-4-Carboxylate Pyridine (63 μl., 0.78 mmol) is added to anti-(2-(3-tritylamino-5-isoxazolyl)-2-methoxyiminoacetic acid prepared in Example 11, in 50 ml. of $CH_2Cl_2$ and the mixture stirred at room temperature for 5 minutes. tert-Butyl-7-aminocephalosporanate (256.0 mg., 0.78 mmol) and diisopropylcarbodiimide (122 μl., 0.78 mmol) are added in that order and the reaction stirred at room temperature for 1.25 hours. The reaction is washed with ice cold 1 N HCl, aqueous $NaHCO_3$, dried ($MgSO_4$) and the solvent removed under reduced pressure. Chromatography of the residue on silica gel (60–200 mesh) using 5–10% $EtOAc-CH_2Cl_2$ as an eluent gives the title compound as a white solid foam (355.7 mg., 62%).

IR (KBr) 3400, 1780, 1725 and 1690 $cm^{-1}$.

NMR ($CDCl_3$) δ 1.55 (S, 9H); 2.04 (S, 3H); 3.30 (d, 1H, J=18.0 Hz); 3.59 (d, 1H, J=18.0 Hz); 4.0 (S, 3H); 4.80 (d, 1H, J=13.0 Hz); 4.98 (d, 1H, J=4.0 Hz); 5.06 (d, 1H, J=13.0 Hz); 5.6–5.9 (m, 3H); 7.32 (S, 15H, and amide NH).

EXAMPLE 14 tert-Butyl 3-Acetoxymethyl-7-[2-(3-Amino-5-Isoxazolyl)-2-anti-Methoxyiminoacetamido]-Ceph-3-em-4-Carboxylate A solution of 36.1 mg. ($4.9 \times 10^{-5}$ mol) of the β-lactam prepared in Example 13, 5 mol. of MeOH and 5 drops of 1 N HCl are stirred at room temperature for 45 minutes. The reaction is partitioned between aqueous $NaHCO_3-CH_2Cl_2$, extracted, dried ($MgSO_4$) and the solvent removed under reduced pressure. The residue is chromatographed on silica gel (60–200 mesh). Initially $CH_2Cl_2$ is used to remove the non-polar material and then 50% $EtOAc-CH_2Cl_2$ is used to elute the product. In this manner the title compound is isolated in 92% yield as a white foam.

IR (KBr) 3420, 3360(sh), 1775, 1720, 1680 and 1620 $cm^{-1}$.

NMR ($CDCl_6$) δ 1.56 (S, 9H); 2.08 (S, 3H); 3.35 (d, 1H, J=18 Hz); 3.61 (d, 1H, J=18 Hz); 4.08 (S, 2H, —$NH_2$); 4.17 (S, 3H); 4.80 (d, 1H, J=13 Hz); 5.04 (d, 1H, J=4 Hz); 5.07 (d, 1H, J=13 Hz); 5.90 (dd, 1H, J=4, 8 Hz); 6.62 (S, 1H); 7.40 (d, 1H, J=8 Hz).

EXAMPLE 15

3-Acetoxymethyl-7-[2-(3-Amino-5-Isoxazolyl)-2-anti-Methoxyiminoacetamido]-Ceph-3-em-4-Carboxylic Acid A solution of 168.6 mg. of the ester prepared in Example 14 in 5 ml. of trifluoroacetic acid and 500 μl. of anisole is stirred at ice bath temperature for 3 hours. The solvent is removed under reduced pressure with the reaction flask in the ice bath. Toluene is added and then removed under reduced pressure with the flask in the ice bath. The residue is then concentrated under reduced pressure at room temperature. Diethyl ether is added and with scratching a solid forms which is triturated with diethyl ether and dried to give the title compound as a light yellow solid (68.4 mg., 42%).

IR (KBr) 3460, 3370, 1775, 1720, 1670 and 1620 $cm^{-1}$.

NMR ($d_6$-DMSO) δ 2.00 (S, 3H); 3.3–3.8 (M, 2H, —$SCH_2$); 4.07 (S, 3H); 4.67 (d, 1H, J=14 Hz); 4.97 (d, 1H, J=14 Hz); 5.11 (d, 1H, J=4 Hz); 5.6–5.8 (M, 1H); 6.57 (S, 1H).

Analysis for: $C_{16}H_{17}N_5O_8S$, Calculated: C, 43.74; H, 3.90; N, 15.94, Found: C, 40.30; H, 3.78; N, 16.35.

| Bacterium | Strain | MIC in μg/ml. |
| --- | --- | --- |
| BA SU | 6633 | 7.81 |
| ST AU | 6538P | 7.81 |
| ST AU | SMITH | 3.90 |
| ST AU | CHP | 15.6 |
| ST AU | 53-180 | 15.6 |
| ES CO | 9637 | 15.6 |
| EN CL | 65-1 | 62.5 |
| SA PA | 11737 | 15.6 |
| EN AE | 13048 | 62.5 |
| KL PN | 10031 | 15.6 |
| PR VU | 6896 | 31.3 |
| PR MI | 9921 | 7.81 |

EXAMPLE 16 tert-Butyl 3-Acetoxymethyl-7-[2-(3-Tritylamino-5-Isoxazolyl)-2-syn-Methoxyiminoacetamido]-Ceph-3-em-4-Carboxylate Isobutyl chloroformate (82 μl., 0.63 mmol) and triethylamine (88 μl., 0.63 mmol) are added in that order to a solution of 246.4 mg. (0.58 mmol) of syn-2-(3-tritylamino-5-isoxazolyl)-2-methoxyiminoacetic acid prepared in Example 12, in 20 ml of dry THF at ice bath temperature and the solution stirred at that temperature for 1 hour. tert-Butyl 7-aminocephalosporanate (229.8 mg., 0.70 mmol) in 10 ml. of dry THF is then added dropwise over 10 minutes and the reaction stirred at ice bath temperature for 1 hour. The reaction is partitioned between ice water-$CH_2Cl_2$, acidified with cold 1 N HCl and extracted. The extracts are washed with aqueous $NaHCO_3$, dried ($MgSO_4$), and the solvent removed under reduced pressure. Chromatography on silica gel (60–200 mesh) using 10% $EtOAc-CH_2Cl_2$ as an eluent gives the title compound as an oil contaminated with tert-butyl 3-acetoxymethyl-7-isobutyloxycarbonylamino-ceph-3-em-4-carboxylate (similar Rf values).

EXAMPLE 17 tert-Butyl 3-Acetoxymethyl-7-[2-(3-Amino-5-Isoxazolyl)-2-syn-Methoxyiminoacetamido]-Ceph-3-em-4-Carboxylate A solution of the mixture obtained in Example 16 in 10 ml. of MeOH containing 20 drops of 1 N HCl is stirred at room temperature for 30 minutes. The reaction is partitioned between aqueous $NaHCO_3-CH_2Cl_2$, extracted, dried ($MgSO_4$) and the solvent removed under reduced pressure. The residue is chromatographed on silica gel (60–200 mesh). Eluting with 10% $EtOAc-CH_2Cl_2$ gives the urethane contaminant (75.2 mg.) as an oil.

IR (neat) 3310, 1775 and 1715 $cm^{-1}$,

NMR ($CDCl_3$) δ 0.96 (d, 6H, J=7 Hz); 1.57 (S, 9H); 1.8–2.6 (M, 1H); 0.10 (S, 3H) 3.38 (d, 1H, J=19 Hz); 3.62 (d, 1 H, J=19 Hz); 3.92 (d, 2H, J=6 Hz); 4.7–5.2 (M, 3H); 5.5–5.8 (M, 2H).

After the urethane contiminant is eluted the polarity of the solvent is changed to 50% $EtOAc-CH_2Cl_2$ and the title compound is collected as a white solid foam (103.4 mg., 35%).

IR (CHCl₃) 3490, 3390, 1780, 1720, 1680 and 1615 cm⁻¹.

NMR (CDCl₃) δ 1.51 (S, 9H); 2.10 (S, 3H); 3.35 (d, 1H, J=20 Hz); 3.65 (d, 1H, J=20 Mz); 3.8–4.1 (M, 2H); 4.20 (S, 3H); 4.82 (d, 1H, J=14 Hz); 5.07 (d, 1H, J=4 Hz); 5.10 (d, 1H, J=14 Hz); 5.93 (dd, 1H, J=4 Hz, 8 Hz); 6.40 (S, 1H); 7.63 (d, 1H, J=8 Hz).

EXAMPLE 18

3-Acetoxymethyl-7-[2-(3-Amino-5-Isoxazolyl)-2-syn-Methoxy-Iminoacetamido]-Ceph-3-em-4-Carboxylic Acid Following the procedure of Example 15, the syn-acid (64.7 mg., 70%) is isolated as a light tan solid.

IR (KBr) 3450, 3360, 1780, 1720, 1670 and 1625 cm⁻¹.

NMR (d₆-DMSO) δ 2.02 (S, 3H); 3.42 (d, 1H, J=16 Hz); 3.67 (d, 1H, J=16 Hz); 3.95 (S, 3H); 4.67 (d, 1H, J=12 Hz); 5.00 (d, 1H, J=12 Hz); 5.15 (d, 1H, J=4 Hz); 5.75 (dd, 1H, J=4 Hz, 8 Hz); 6.01 (S, 1H); 9.80 (d, 1H, J=8 Hz).

Analysis for: $C_{16}H_{17}N_5O_8S$, Calculated: C, 43.74; H, 3.90; N, 15.94. Found: C, 42.63; H, 3.77; N, 13.94.

| Bacterium | Strain | MIC in μg/ml. |
|---|---|---|
| BA SU | 6633 | 0.488 |
| ST AU | 6538P | 1.95 |
| ST AU | SMITH | 0.488 |
| ST AU | CHP | 7.81 |
| ST AU | 53-180 | 3.90 |
| ES CO | 9637 | 0.488 |
| EN CL | 65-1 | 1.95 |
| SA PA | 11737 | 0.488 |
| EN AE | 13048 | 31.3 |
| KL PN | 10031 | 0.488 |
| BO BR | 4617 | 250.0 |
| PR VU | 6896 | 0.976 |
| AC CA | 9955 | 125.0 |
| PR MI | 9921 | 0.488 |

The product of Example 18 was reexamined by the microdilution method of tube dilution assay employing Mueller Hinton Broth whereby standardized cultures were introduced into serially diluted antibiotic from Example 18. The results obtained were compared with Cefotaxime as a standard cephalosporin as follows:

| Bacterium | Strain | Cefotaxime MIC in μg/ml. | Example 18 MIC in μg/ml. |
|---|---|---|---|
| BA SU | 6633 | 0.488 | 1.95 |
| ST AU | 209P | 0.488 | 0.244 |
| ST AU | SMITH | 0.244 | 0.244 |
| ST AU | CHP | 3.90 | 3.90 |
| ST AU | 53-180 | 0.976 | 0.488 |
| KL PN | 10031 | 0.00006 | 0.0152 |
| ES CO | 9637 | 0.0038 | 0.122 |

| Bacterium | Strain | Cefotaxime MIC in μg/ml. | Example 18 MIC in μg/ml. |
|---|---|---|---|
| SA PA | 11737 | 0.0076 | 0.488 |
| EN AE | 13048 | 0.0152 | 0.976 |
| BO BR | 4617 | 15.6 | 125.0 |
| PR VU | 6896 | 0.00023 | 0.122 |
| PR MI | 9921 | 0.0019 | 0.122 |
| HE SP | 9955 | 15.6 | 62.5 |
| PS AE | 10145 | 3.90 | 125.0 |
| ES IN | 65-1 | 0.0038 | 0.488 |

What is claimed is:

1. A compound of the formula:

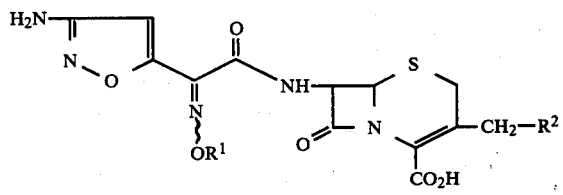

in which:
R¹ is H, alkyl of 1 to 4 carbon atoms, alkenyl of 2 to 4 carbon atoms, alkynyl of 2 to 4 carbon atoms, arylalkyl of 7 to 10 carbon atoms, 2-carboxyprop-2-yl, carboxymethyl, alkanoyl of 2 to 4 carbon atoms or α-phenylalkanoyl of 8 to 10 carbon atoms;
R² is H, hydroxy, alkanoyloxy of 2 to 6 carbon atoms, carbamoyloxy,

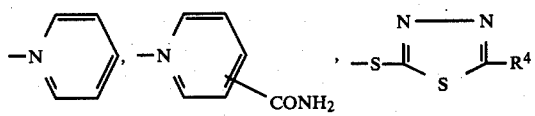

where
R⁴ is hydrogen or alkyl of 1 to 4 carbon atoms or

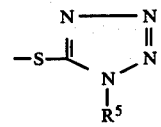

where
R⁵ is hydrogen or alkyl of 1 to 4 carbon atoms, vinyl, sulfonyloxymethyl or carboxymethyl;
or a pharmaceutically acceptable salt thereof.

2. The compound of claim 1 which is 3-acetoxymethyl-7-[2-(3-amino-5-isoxazolyl)-2-syn-methoxyiminoacetamido]-ceph-3-em-4-carboxylic acid or a pharmaceutically acceptable salt thereof.

3. The compound of claim 1 which is 3-acetoxymethyl-7-[2-(3-amino-5-isoxazolyl)-2-anti-methoxyiminoacetamido]-ceph-3-em-4-carboxylic acid or a pharmaceutically acceptable salt thereof.

* * * * *